(12) United States Patent
Choi et al.

(10) Patent No.: US 10,241,574 B2
(45) Date of Patent: Mar. 26, 2019

(54) WEARABLE BIOSIGNAL INTERFACE AND METHOD THEREOF

(71) Applicant: Samsung Electronics Co., Ltd., Suwon-si (KR)

(72) Inventors: Chang Mok Choi, Suwon-si (KR); Sang Joon Kim, Suwon-si (KR); Seung Keun Yoon, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 78 days.

(21) Appl. No.: 14/913,085

(22) PCT Filed: May 8, 2014

(86) PCT No.: PCT/KR2014/004073
§ 371 (c)(1),
(2) Date: Feb. 19, 2016

(87) PCT Pub. No.: WO2015/026047
PCT Pub. Date: Feb. 26, 2015

(65) Prior Publication Data
US 2016/0202759 A1    Jul. 14, 2016

(30) Foreign Application Priority Data
Aug. 20, 2013    (KR) .................. 10-2013-0098476

(51) Int. Cl.
*G06F 1/16* (2006.01)
*G06F 3/01* (2006.01)
(Continued)

(52) U.S. Cl.
CPC .............. *G06F 3/015* (2013.01); *G06F 1/163* (2013.01); *G06F 1/1694* (2013.01); *G06F 3/017* (2013.01); *G06F 3/038* (2013.01); *G06F 3/0346* (2013.01)

(58) Field of Classification Search
None
See application file for complete search history.

(56) References Cited

U.S. PATENT DOCUMENTS 5,832,296 A * 11/1998 Wang .................... G06F 3/0338
340/539.22
2006/0149146 A1    7/2006 Schmidt et al.
(Continued)

FOREIGN PATENT DOCUMENTS

CN    1488115 A    4/2004
CN    100440310 C    12/2008
(Continued)

OTHER PUBLICATIONS

European Search Report dated Jul. 11, 2017 in Corresponding European Patent Application No. 14838613.9 (11 pages in Englsih).
(Continued)

*Primary Examiner* — Gustavo D Polo
(74) *Attorney, Agent, or Firm* — NSIP Law

(57) ABSTRACT

A wearable biosignal interface and operation method of the wearable biosignal interface is provided wherein the wearable biosignal interface may perceive a motion unintentionally performed by a user and ignore a biosignal obtained thereby and thus, improve accuracy of a bio-based determination of an intention of the user for operating a device.

20 Claims, 5 Drawing Sheets

(51) Int. Cl.
*G06F 3/038* (2013.01)
*G06F 3/0346* (2013.01)

(56) References Cited

U.S. PATENT DOCUMENTS

2006/0281979 A1 12/2006 Kim et al.
2010/0145171 A1  6/2010 Park et al.
2012/0172733 A1  7/2012 Park
2012/0184826 A1  7/2012 Keenan et al.
2012/0259182 A1 10/2012 Kim et al.

FOREIGN PATENT DOCUMENTS

| KR | 10-2003-0040316 A | 5/2003 |
| KR | 10-2006-0069985 A | 6/2006 |
| KR | 10-2007-0000848 A | 1/2007 |
| KR | 10-2007-0109044 A | 11/2007 |
| KR | 10-2009-0027390 A | 3/2009 |
| KR | 10-2009-0032537 A | 4/2009 |
| KR | 10-2010-0027375 A | 3/2010 |
| KR | 10-2011-0062558 A | 6/2011 |
| KR | 10-2011-0123708 A | 11/2011 |
| KR | 10-2012-0014233 A | 2/2012 |
| KR | 10-2012-0111030 A | 10/2012 |
| KR | 10-2012-0133350 A | 12/2012 |
| WO | WO 2008/073801 A2 | 6/2008 |

OTHER PUBLICATIONS

International Search Report dated Aug. 7, 2014 in counterpart International Application No. PCT/KR2014/004073 (2 pages in English; 2 pages in Korean).
Chinese Office Action dated Jan. 2, 2018 in corresponding Chinese Patent Application No. 201480044084.7 (8 pages in English and 7 pages in Chinese).

\* cited by examiner

WEARABLE BIOSIGNAL INTERFACE AND METHOD THEREOF

CROSS-REFERENCE TO RELATED APPLICATIONS

This application is a U.S. National Stage Application of International Application No. PCT/KR2014/004073, filed on May 8, 2014, which claims the benefit under 35 USC 119(a) of Korean Patent Application No. 10-2013-0098476 filed on Aug. 20, 2013, in the Korean Intellectual Property Office, the entire disclosure of which is incorporated herein by reference for all purposes.

BACKGROUND

1. Field

The following description relates to a wearable biosignal interface and an operation method thereof, and to an apparatus for controlling an external device and a method of controlling an external device using a wearable apparatus.

2. Description of Related Art

Recently, wearable-type mobile devices are emerging at an accelerated rate amid the proliferation of smartphones. A wearable-type mobile device may include a separate screen for displaying information obtained by a smartphone through a wireless data network, allowing its user to process data without directly viewing the screen of the smartphone.

A gesture recognized by an accelerometer or a biosignal sensor may be used to operate the wearable mobile device. However, operating the wearable mobile device based only on the gesture may increase a probability of misrecognizing the intention of the user. For example, in a wearable mobile device designed to be operated by recognizing a hand gesture, a movement of the arm connected to the hand may be recognized as a hand gesture, misinterpreting the intention of the user in operating the wearable mobile device.

Accordingly, a wearable mobile device model that recognizes an intention of a user with a greater precision is desirable to improve user experience.

SUMMARY

In one general aspect, there is a provided a wearable biosignal interface including a motion sensor configured to obtain a first signal based on a motion of a target, a biosignal sensor disposed on the target and configured to obtain a second signal from the target, and a determination controller configured to determine a validity of the second signal based on the first signal.

The second signal may include biological information obtained by one or more biosensor in contact with skin of the target.

The determination controller may be configured to determine the second signal to be valid in response to a magnitude of the first signal satisfying a first threshold value.

The determination controller may be configured to identify an interval during which a magnitude of the first signal is less than or equal to a first threshold value and to determine a signal, among a plurality of second signals obtained by the biosignal sensor in the identified interval, to be a valid second signal.

The determination controller may be configured to determine the first threshold value based on a magnitude of the second signal.

The determination controller may be configured to determine the second signal to be invalid, irrespective of the first signal, in response to the magnitude of the second signal not satisfying a second threshold value.

In response to a determination that the second signal is valid, the determination controller may be configured to operate in an active mode and to control an external device based on the second signal.

In another general aspect, an operation method of a wearable biosignal interface may involve using a motion sensor to obtain a first signal based on a motion of a target, using a biosignal sensor disposed on the target to obtain a second signal, and determining a validity of the second signal based on the first signal.

The second signal may include biological information obtained by one or more biosensor in contact with skin of the target.

The determining of the validity may involve determining the second signal to be valid in response to a magnitude of the first signal satisfying a first threshold value.

The determining of the validity may involve identifying an interval during which a magnitude of the first signal is less than or equal to a first threshold value, and determining a signal, among second signals obtained by the biosignal sensor in the identified interval, to be a valid second signal.

The determining of the validity may further include determining a first threshold value based on a magnitude of the second signal.

The determining of the validity may involve determining the second signal to be invalid, irrespective of the first signal, in response to a magnitude of the second signal not satisfying a second threshold value.

The general aspect of the method may further involve operating in an active mode and controlling an external device based on the second signal, in response to the second signal being determined to be valid.

In another general aspect, an apparatus including a motion sensor configured to detect movement of a target, a second sensor configured to detect biological information of the target, and a controller configured to determine an interval of stability from the movement of the target detected by the motion sensor, to determine whether a magnitude of a biological signal obtained during the interval is less than or equal to a first threshold value, and to identify a command for controlling another device in response to the magnitude being less than or equal to the first threshold value.

The interval may be determined by extracting a first processed signal from the detected movement of the target, and the biological signal may be obtained by extracting a second processed signal from the biological information obtained by the second sensor, the second sensor comprising one or more biosensor.

The interval may correspond to a time duration in which a magnitude of the first processed signal is less than or equal to a second threshold value.

The general aspect of the apparatus may further include a transmission unit configured to transmit the command to the another device, and the determination controller may be configured to identify the command based on the second processed signal.

In response to a determination that the magnitude of the biological signal is greater than the first threshold value, the apparatus may be configured not to transmit a command based on the biological information obtained during the interval.

Other features and aspects will be apparent from the following detailed description, the drawings, and the claims.

Figure 1:
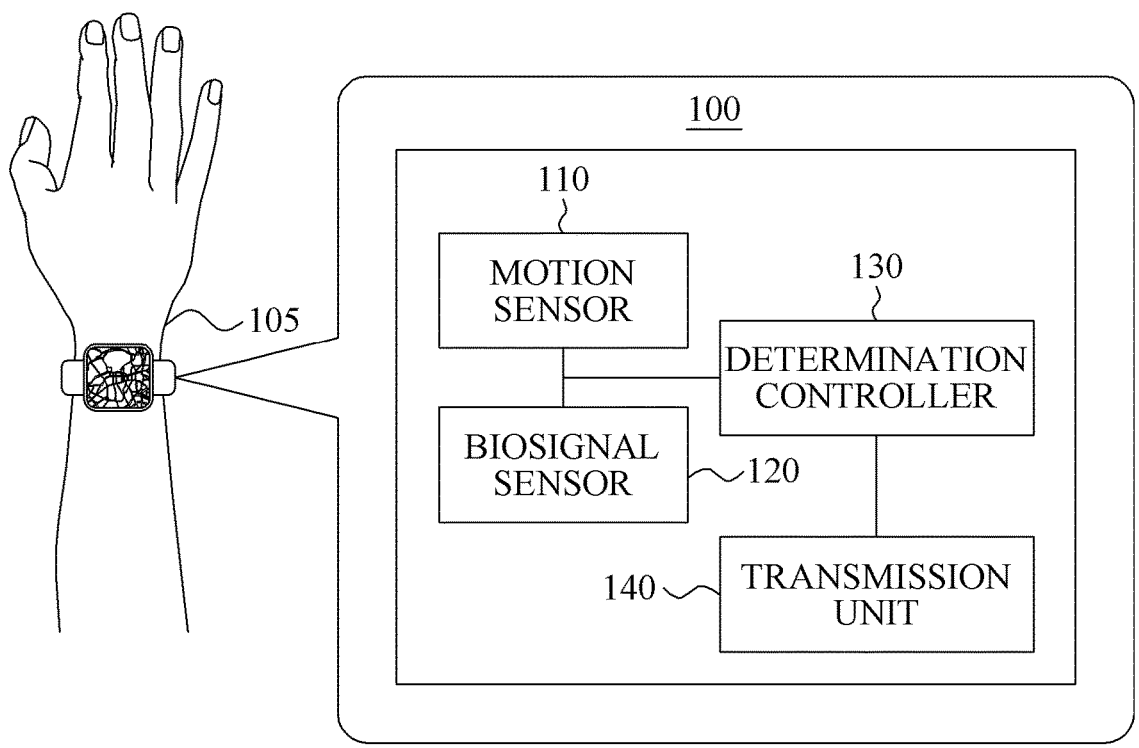
FIG. 1 is a diagram illustrating an example of a wearable biosignal interface.

Throughout the drawings and the detailed description, unless otherwise described, the same drawing reference numerals will be understood to refer to the same elements, features, and structures. The relative magnitude and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

As described herein, a sensor may refer to a sensor or a plurality of sensors that may be attached to a target to be in contact therewith or disposed thereon so as to obtain a signal generated from the target or to detect a motion of the target.

For example, a sensor may include a biosensor that may be attached to a body part of a living being or living organism such as, for example, a wrist or a forearm of a person, in order to obtain a biological or physiological signal. For example, a biosensor may be able to detect signals generated by muscle contraction or muscle relaxation of a body part, such as a wrist or a heart. Herein, such a sensor may refer to as a biosignal sensor. A biosignal sensor may detect biological information from a target and may convert the biological information into a signal waveform to generate a biosignal. Such a biosignal sensor may include a photo sensor, a piezoelectric sensor, a force sensor, an electromyogram (EMG) sensor, and the like.

Herein, a muscle may refer to a striated muscle, a cardiac muscle or a smooth muscle, and may refer to a muscle group, a number of muscle groups in a body region, bundles of muscle fibers and the like. For instance, an arm may include several different muscle groups, including a tricep, a bicep and a brachioradialis.

A sensor may include an acceleration sensor, a gyro sensor, a geomagnetic sensor, and a Global Positioning System (GPS) sensor. Such a sensor may directly or indirectly monitor a motion performed by the living target and may obtain a signal associated with the motion performed by the living target. Hereinafter, the sensor described above will be referred to as a motion sensor.

To control an external device using a biosignal obtained by a biosignal sensor, an example of a wearable biosignal interface may ignore a biosignal in the event that a magnitude of a signal associated with a motion of a target exceeds a threshold value. Conversely, the wearable biosignal interface may receive the biosignal in the event that the magnitude of the signal associated with the motion of the target is less than or equal to the threshold value.

The wearable biosignal interface may make a determination as to whether a motion is unintentionally or spontaneously made by a user, and may ignore a biosignal obtained as a result of the unintentional or spontaneous motion. Using this approach, the accuracy of determination regarding the intention of the user may be improved.

FIG. 1 is a diagram illustrating an example of a wearable biosignal interface 100.

Referring to FIG. 1, the example of the wearable biosignal interface 100 include a motion sensor 110, a biosignal sensor 120, a determination controller 130, and a transmission unit 140.

The motion sensor 110 may detect a motion of a target 105 and may obtain a first signal. For instance, the first signal may include an acceleration signal, a rotation signal, a bearing signal, and a coordinate signal. These signals may be associated with velocity variance based on a motion of the target 105.

The motion sensor 110 may monitor a motion of the target 105 and may receive the first signal recognizing a movement of the wearable biosignal interface 100 associated with the motion. Also, the motion sensor 110 may identify a gesture performed by the target 105 by obtaining a second signal after obtaining a first signal associated with an identified gesture.

The motion sensor 110 may include, for example, an acceleration sensor. Such a motion sensor 110 may convert an acceleration signal corresponding to the obtained first signal into a velocity component by calculating an integral of the acceleration signal. The motion sensor 110 may determine one or more numerical values indicating a magnitude of a motion of the target 105.

In the event that the target 105 is an arm that is flexed in any direction, the motion sensor 110 may obtain a first signal associated an "arm motion" based on the flexing. Also, the motion sensor 110 may measure a magnitude of the obtained first signal and may measure a magnitude of a velocity of the "arm motion."

The motion sensor 110 may include a gyrosensor. Using a gyrosensor, such a motion sensor 110 may detect a rotation signal corresponding to the first signal.

The target 105 may be an arm. In the event that the arm performs a large rotation motion, the motion sensor 110 may obtain a first signal associated with the "arm rotation" based on the rotating motion of the arm. In addition, the motion sensor 110 may measure a magnitude of the obtained first signal and may measure a magnitude of a rotational velocity of the "arm rotation."

The motion sensor 110 may include a geomagnetic sensor or a GPS sensor. Using the geomagnetic sensor or the GPS sensor, such a motion sensor 110 may detect a bearing signal or a coordinate signal corresponding to the first signal.

The motion sensor 110 may be fixed to a form of a bracelet fastened onto the target 105, along with the biosignal sensor 120.

The biosignal sensor 120 may be in contact with the target 105 and may obtain a second signal from the target 105. In the illustrated example, the biosignal sensor 120 directly contact the skin of the target 105. However, in another example, the biosignal sensor 120 may be disposed on the target 105 indirectly, such as through a clothing that covers the skin. The second signal may be a biosignal associated with biological information such as, for example, muscle contraction and muscle relaxation occurring in the target 105. The second signal may be a bio-electric/magnetic signal, a bio-impedance signal, and a bio-mechanical signal generated in association with a muscle.

The biosignal sensor 120 may be in contact with the target 105 and may obtain the second signal generated by at least one of muscle contraction and muscle relaxation. In the event that the target 105 is a wrist, the biosignal sensor 120 may detect the second signal generated by the muscle contraction or muscle relaxation of the wrist.

The target 105 may be a wrist, a forearm, a face, a neck, or the like of a living being, and a muscle that generates a second signal may be located within the portion of body.

The biosignal sensor 120 may include at least one biosensor that may detect the second signal from a muscle of the target 105, and may monitor the contraction or relaxation of the muscle using the at least one biosensor. The biosensor may be a photo sensor, a piezoelelctric sensor, a force sensor, an electromyogram (EMG) sensor, and the like.

For example, the biosignal sensor 120 may include the photo sensor. Using the photo sensor, such a biosignal sensor 120 may obtain the second signal associated with a status of the target 105, based on light scattering.

The biosignal sensor 120 may include a piezoelelctric sensor or a force sensor. Using a piezoelelctric sensor or a force sensor, such a biosignal sensor 120 may obtain a second signal associated with an extension and/or contraction of a muscle of the target 105.

The biosignal sensor 120 may include an EMG sensor. Using an EMG sensor, a biosignal sensor may obtain a second signal associated with the muscle contraction or relaxation of a heart muscle of a target 105.

The biosignal sensor 120 may be fixed to the bracelet fastened onto the target 105, along with the motion sensor 110. A sensing surface of the biosignal sensor 120 may be fixed to the bracelet to be in a direct contact with the target 105. On the sensing surface, the at least one biosensor may be arranged to detect the second signal generated from a target 105. Using the biosignal sensor 120, the bracelet may broadly detect a second signal such as the bio-electric/magnetic signal, the bio-impedance signal, and the bio-mechanical signal over an area of the body of the target 105.

The bracelet may be fastened onto the target 105 by being wrapped around a wrist muscle over the skin, for example. The bracelet may be fastened onto the target 105 by covering the wrist muscle with an area of the bracelet, for example, the sensing surface, in which one or more biosignal sensor 120 is arranged. Using one or more biosensors, the biosignal sensor 120 may collect a second signal from throughout an entire area of the wrist muscle of the target 105.

The determination controller 130 may determine a validity of the second signal based on the first signal. The determination controller 130 may determine whether the second signal obtained using the biosignal sensor 120 is generated from the target 105 due to an intentional motion or a motion incidentally generated from the target 105 due to an unintentional or spontaneous motion made irrespective of an intention of a user to operate an external device.

The determination controller 130 may determine the second signal to be valid when a magnitude of the first signal satisfies a first threshold value.

The first threshold value may be a reference value used to determine the intentional motion of the target 105. The first threshold value may be determined as an average value of magnitudes of first signals obtained when the user moves a muscle for an actual operation.

The determination controller 130 may determine the first threshold value based on a magnitude of the second signal to be obtained. The determination controller 130 may determine the first threshold value for an operation involving a large motion of the target 105 to be greater in proportion to the magnitude of the second signal. Accordingly, the second signal generated by an intentional motion may not be ignored due to a low threshold value.

For example, the determination controller 130 may determine the first threshold value for a quick display shift operation of a display apparatus for which a relatively greater second signal is generated to be greater than the first threshold value for an ON/OFF operation of an illumination apparatus for which a relatively smaller second signal is generated.

To determine a validity of a second signal, the determination controller 130 may identify an interval during which the magnitude of the first signal is less than or equal to the first threshold value and may determine a signal, among the second signals obtained during the identified interval, to be a valid second signal. The determination controller 130 may determine, to be valid, the second signal obtained in the interval during which the magnitude of the first signal is less than or equal to the first threshold value and a small motion of the target 105 is performed.

In the event that the magnitude of the second signal does not satisfy a second threshold value, the determination controller 130 may determine the second signal to be invalid, irrespective of the first signal. The second threshold value may be a reference value used to determine a second signal that is valuable as information. The second threshold value may be set as an averaged minimum value obtained based on data obtained by simulations in which users moved their muscles to initiate an actual operation.

In response to the magnitude of the second signal being less than or equal to the determined second threshold value, the determination controller 130 may determine whether the target 105 moves intentionally or unintentionally to be indefinite and invalidate the second signal. Conversely, in response to the magnitude of the second signal being greater than the determined second threshold value, the determination controller 130 may further determine whether the magnitude of the first signal satisfies the first threshold value and may determine the validity of the second signal.

Based on the determination, the determination controller 130 may operate in an active mode in response to the second signal being determined to be valid and may allow an external device to be controlled based on the second signal.

An external device may refer to a device controlled by a command signal, such as a mobile device, a television (TV) screen, a digital versatile disc (DVD) player, a radio, a heating thermostat, a vehicle door, and the like. The command signal may be generated in association with a valid second signal of the wearable biosignal interface 100.

In the event that the magnitude of the first signal is less than or equal to the first threshold value and the magnitude of the second signal is greater than the second threshold value, the determination controller 130 may shift a mode of the wearable biosignal interface 100 to the active mode and may allow the external device to be controlled based on the second signal. Thus, the accuracy of determining an intention of a user to operate the device may be improved.

To control the external device after the shift to the active mode, the wearable biosignal interface 100 may transmit the command signal based on the second signal determined to be valid to an appliance or a device in order to enable the external device to perform a control operation, using the transmission unit 140. For example, the wearable biosignal interface 100 may transmit a command signal to an appliance such as a TV, an air conditioner, a computer, a refrigerator, and the like, or to a living environment controlling device such as a light, a curtain, a window, a door lock device, and the like. The signal transmission may enable the external device to perform a control operation of the appliance or device such as an ON/OFF operation, an open/close operation, and the like, in accordance with the command signal.

In another example, the wearable biosignal interface 100 may use a valid second signal (or a second signal determined to be valid) as a signal of a remote controller of a vehicle to start the vehicle or as an ID signal to make a payment.

In yet another example, the wearable biosignal interface 100 may use the valid second signal for an interaction control with a computer, or a signal to edit a file stored on the computer or to move a page for a presentation.

The wearable biosignal interface 100 may detect and invalidate a biosignal generated by the unintentional motion of the target 105; thus, the wearable biosignal interface 100 may optimally avoid a control error for the external device.

The wearable biosignal interface 100 may identify a biosignal generated only when the target 105 is under a certain level of stability, and may use the biosignal obtained during the stable condition to control an external device; thus, the wearable biosignal interface 100 may provide a precise determination of the user's intention for operating the external device.

FIG. 2A through FIG. 2D are diagrams illustrating examples of methods of determining a second signal as a valid signal based on a first signal and a second signal.

Figure 2A:
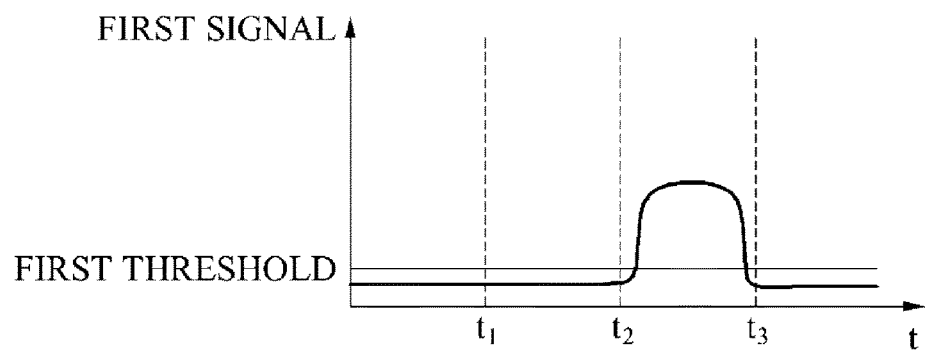
FIG. 2A through FIG. 2D are diagrams illustrating an example of a method of determining the validity of a signal based on a first signal and a second signal.

FIG. 2A is a diagram illustrating an example of a first signal obtained using a motion sensor 110 of FIG. 1 of a wearable biosignal interface 100 of FIG. 1. When a target 105 of FIG. 1 performs a rapid motion, such as a motion of flexing an arm, in a interval from $t_2$ to $t_3$, the motion sensor 110 may obtain the first signal having a magnitude measured to be great in the interval from $t_2$ to $t_3$. The first signal obtained in the interval from $t_2$ to $t_3$ may be greater than a first threshold value used as a reference value to determine an intentional motion of the target 105.

Figure 2B:
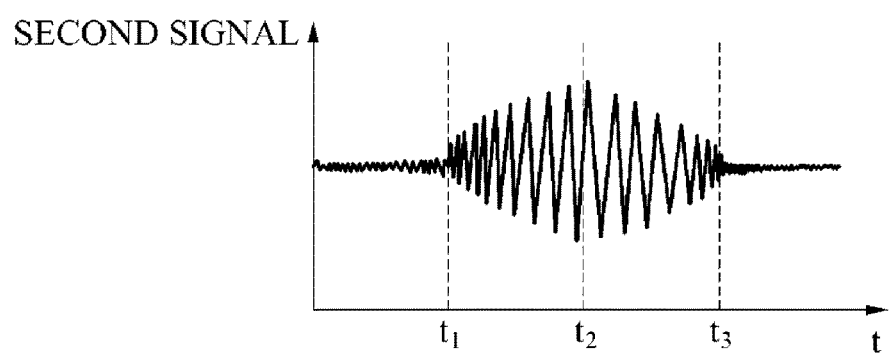

FIG. 2B is a diagram illustrating an example of a second signal obtained by a biosignal sensor 120 of FIG. 1 of a wearable biosignal interface 100 of FIG. 1. As illustrated in FIG. 2B, the obtained second signal may be in a form of an analog sine waveform and may have a greater waveform in a interval from $t_1$ to $t_3$ during which muscles of an arm are tense due to the flexing of the arm.

Figure 2C:
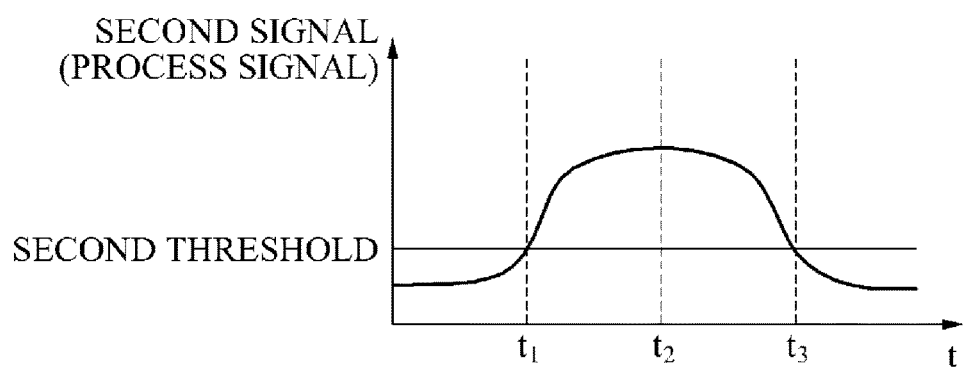

FIG. 2C is a graph illustrating an example in which a determination controller 130 of FIG. 1 of a wearable biosignal interface 100 of FIG. 1 processes magnitudes of the obtained second signals and compares the magnitudes. The determination controller 130 may plot, based on the second signal of FIG. 2B, a parabola in which an inclination increases drastically after a point $t_1$ at which a waveform becomes larger and the inclination decreases drastically after a point $t_3$ at which the waveform becomes smaller.

The second signal in the interval from $t_1$ to $t_3$ may be obtained when satisfying a second threshold value used as a reference value to determine a second signal that is valuable as information.

Figure 2D:
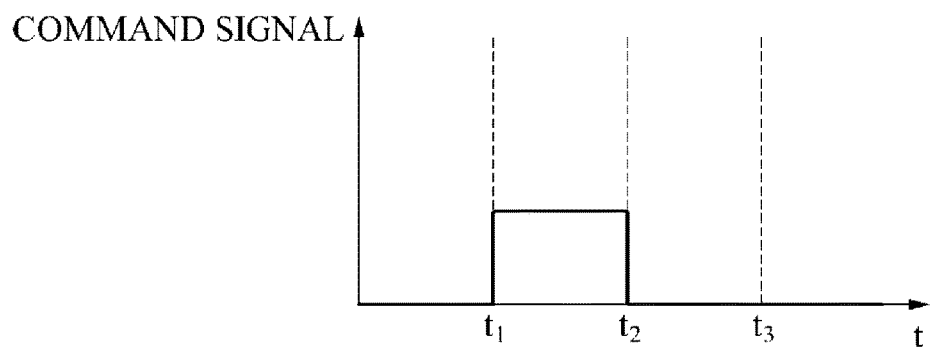

FIG. 2D illustrates an example of a method of determining, by a determination controller 130 of FIG. 1, a validity of a second signal based on a first signal and a second signal.

The determination controller 130 may invalidate the second signal obtained in the interval from $t_2$ to $t_3$ in which the first signal exceeding the first threshold value is obtained. Also, the determination controller 130 may invalidate the second signal obtained during an interval before $t_1$ and after $t_3$ during which the second signal less than or equal to the second threshold value is obtained.

As shown in FIG. 2D, the determination controller 130 may determine the second signal obtained in of the interval from $t_1$ to $t_2$ to be a valid signal and may enable a command signal to be generated to control an external device during the interval.

The wearable biosignal interface 100 may operate, using the second signal, an external device such as a mobile device, a TV screen, a DVD, a radio, a heating thermostat, a vehicle door, and the like. The wearable biosignal interface 100 may allow the operation of the external device, using the second signal, only when the magnitude of the first signal decreases to be less than or equal to the first threshold value due to a small motion performed by a user in order to improve the accuracy of the wearable biosignal interface 100 in determining an intention of a user for operation.

The wearable biosignal interface 100 may also allow the operation of the external device in response of the magnitude of the second signal satisfying the second threshold value, indicating that the second signal includes valuable information.

Figure 3:
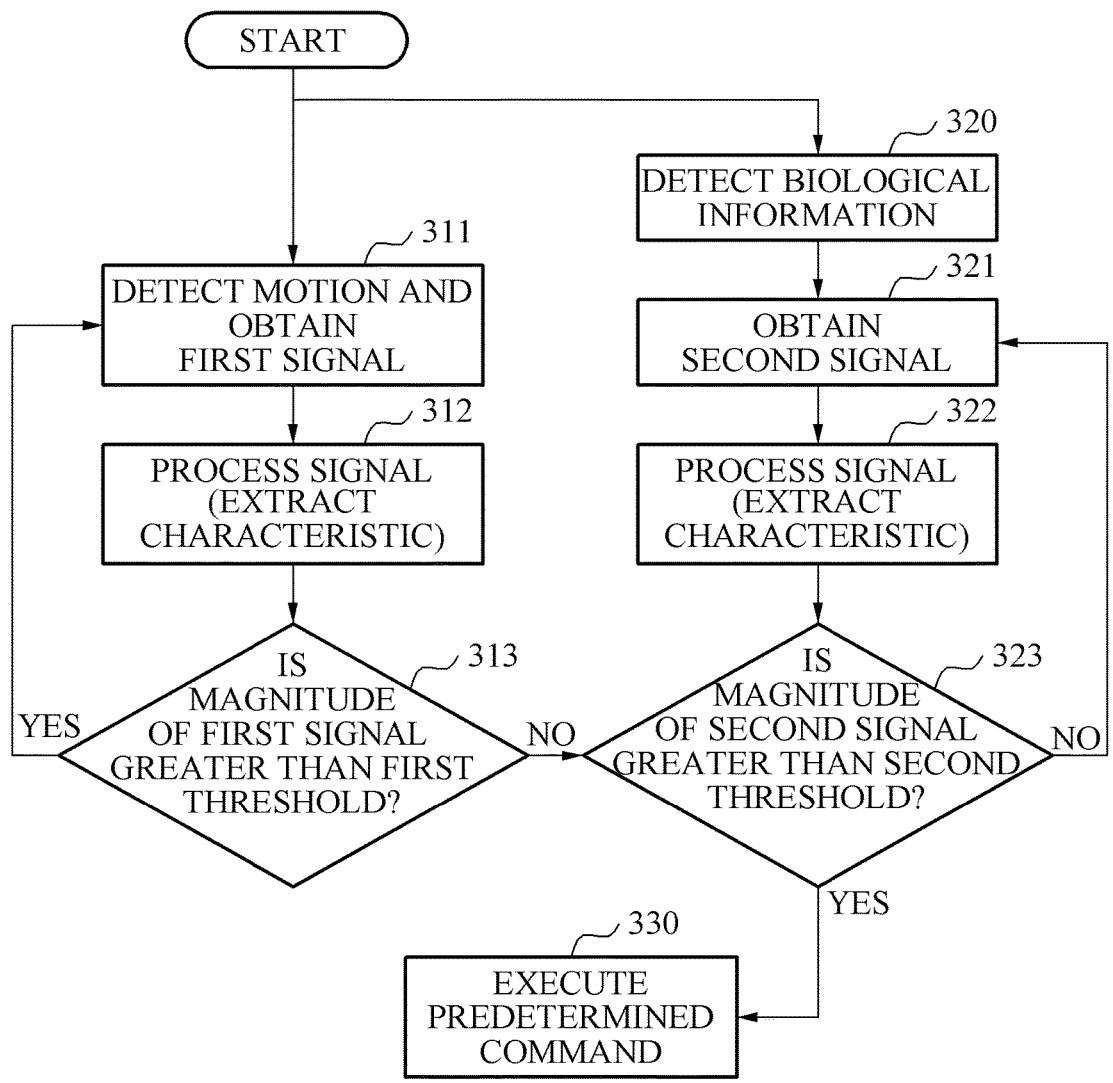
FIG. 3 is a diagram illustrating an example of a method of performing a command given to an external device, using a magnitude of a first signal and a magnitude of a second signal.

FIG. 3 is a diagram illustrating an example of a method of performing a command given to an external device, using a magnitude of a first signal and a magnitude of a second signal.

Referring to FIG. 3, in 311, a motion sensor of a wearable biosignal interface may detect a motion of a target, and the motion sensor may obtain a first signal. For example, the motion sensor may detect and obtain a first signal associated with the flexing of an arm. In this example, the arm is the target from which signals can be detected.

In 312, the wearable biosignal interface may process the first signal obtained by the motion sensor and may extract a characteristic. For example, wearable biosignal interface may extract the magnitude of the first signal corresponding to a characteristic associated with a speed at which an arm is flexed.

In 313, the wearable biosignal interface may determine whether the magnitude of the first signal is greater than a first threshold value. For example, the wearable biosignal interface may determine a magnitude of a first signal obtained in response to a user moving a muscle to actually operate an external device to be the first threshold value, and may compare the first threshold value to magnitudes of the obtained first signals.

Also, in 313, the wearable biosignal interface may identify an interval during which the magnitude of the first signal is less than or equal to the first threshold value.

In response to a determination that the magnitude of the first signal is greater than the first threshold value, for example, in a 'Yes' direction from 313, the wearable biosignal interface may ignore the second signal obtained in the same interval during which the first signal is obtained. Also, the wearable biosignal interface may re-obtain the first signal in 311.

Conversely, in response to a determination that the magnitude of the first signal is less than or equal to the first threshold value, for example, in a 'No' direction of 313, the wearable biosignal interface may proceed to 323, as described later. The wearable biosignal interface may determine whether the second signal is valid based on a result of comparing the magnitude of the second signal obtained in the same interval during which the first signal is obtained to the second threshold value.

If the magnitude of the second signal is less than the second threshold value, in 321, a biosignal sensor of the wearable biosignal interface may detect and may obtain a second signal from the target. For example, the biosignal sensor may obtain the second signal in response to detecting a tenseness of the muscles of the arm due to a flexing of the arm. The second signal may be obtained from the biological information detected by the biosignal sensor in 320.

In 322, the wearable biosignal interface may process the second signal obtained by the biosignal sensor 320 and may extract a characteristic of the second signal. For example, the wearable biosignal interface may extract a magnitude of the second signal corresponding to a characteristic associated with the tension in the flexed arm.

In 323, the wearable biosignal interface may determine whether the magnitude of the second signal is greater than a second threshold value. For example, the wearable biosignal interface may determine a reference value of the magnitude of the second signal, which may be a valuable information for determining the second threshold value, and may compare the second threshold value to magnitudes of the obtained second signals. In 323, the wearable biosignal interface may determine a signal obtained in the identified interval during which the magnitude of the first signal is less than or equal to the first threshold value to be a valid second signal.

In the event that the magnitude of the second signal is less than or equal to the second threshold value, for example, a 'No' direction of 323, the wearable biosignal interface may ignore the obtained second signal irrespective of a determination made in 313. Also, the wearable biosignal interface may re-obtain the second signal in 321.

Conversely, in the event that the magnitude of the second signal is greater than the second threshold value, for example, in a 'Yes' direction of 323, the wearable biosignal interface may ultimately determine the second signal to be valid based on a result of determination in 313 and may proceed to 330 to execute the predetermined command.

Operations described in the foregoing include using a motion sensor to obtain a first signal in 311, and using a biosignal sensor to obtain a second signal in 321. However, it may be possible to perform 321 prior to or concurrent with 311.

In 330, the wearable biosignal interface may execute a command based on the second signal determined to be valid. In 330, the wearable biosignal interface may operate in an active mode and may allow an external device to be controlled based on the second signal. Using the second signal that is determined to be valid, the wearable biosignal interface may operate an external device such as a mobile device, a TV screen, a DVD player, a radio, a heating thermostat, a vehicle door and the like.

Hereinafter, operations of a wearable biosignal interface 100 according to another example will be described with reference to FIG. 4.

Figure 4:
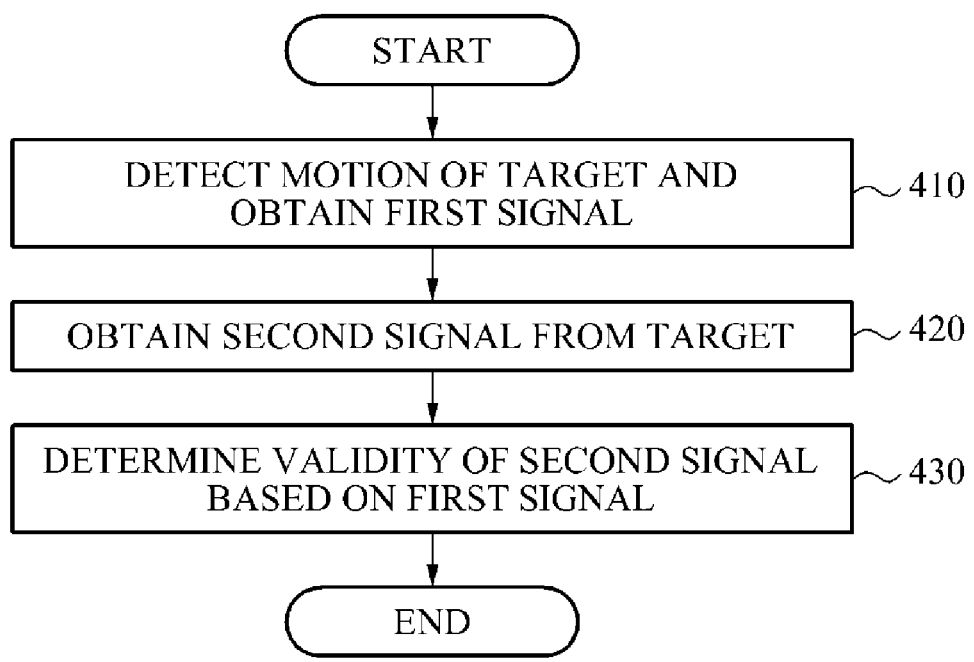
FIG. 4 is a flowchart illustrating an example of a method of operating a wearable biosignal interface.

FIG. 4 is a flowchart illustrating an example of an operation method of a wearable biosignal interface 100.

In 410, the wearable biosignal interface 100 may detect a motion of a target 105 of FIG. 1 and may obtain a first signal. The first signal may be, for example, an acceleration signal, a rotation signal, a bearing signal, a coordinate signal, and the like, that is associated with a velocity variance based on the motion of the target 105. In 410, the wearable biosignal interface 100 may monitor, using a motion sensor 110 of FIG. 1, the motion of the target 105 and may receive the first signal to perceive a movement involved with the motion. For example, the wearable biosignal interface 100 may identify a gesture performed by the target 105 in response to obtaining a biosignal, and may obtain the first signal associated with the identified gesture.

For example, the motion sensor 110 may include an acceleration sensor. By applying integral calculus, the motion sensor 110 may convert an acceleration signal obtained by the acceleration sensor as the first signal into its velocity component. Based on the calculation, the wearable biosignal interface 100 may numerically indicate a magnitude of a motion of the target.

For example, in the event that the target 105 is an arm that is flexed, the wearable biosignal interface 100 may obtain the first signal associated with an "arm motion" based on the flexing of the arm. Also, the wearable biosignal interface 100 may measure the magnitude of the obtained first signal and may measure a velocity magnitude of the "arm motion."

The motion sensor 110 may include a gyrosensor. For example, using the gyrosensor, the wearable biosignal interface 100 may measure a rotation signal corresponding to the first signal.

In one example, target 105 may be an arm, and the arm may be performing a large rotation. The wearable biosignal interface 100 may obtain the first signal associated with the arm rotation based on the detected movement of the arm. Also, the wearable biosignal interface 100 may measure the magnitude of the obtained first signal and/or may measure the magnitude of the anglular velocity of the arm rotation.

The motion sensor 110 may include a geomagnetic sensor or a GPS sensor. Using the geomagnetic sensor or the GPS sensor, the motion sensor 110 may measure a bearing signal or a coordinate signal corresponding to the first signal.

According to an example, the motion sensor 110 may be fixed to a form of a bracelet fastened onto the target 105, along with a biosignal sensor 120.

The wearable biosignal interface 100 may be in contact with the target 105 and may obtain a second signal from the target 105. In this example, the second signal may be a biosignal associated with biological information such as muscle contraction and muscle relaxation that is occurring in the target 105. The second signal may be a bio-electric/magnetic signal, a bio-impedance signal, and/or a bio-mechanical signal generated in association with a muscle movement or muscle tone.

In 420, the wearable biosignal interface 100 may be in contact with the target 105 through the biosignal sensor 120 and may obtain the second signal generated by at least one of muscle contraction and muscle relaxation. In an example in which the target 105 is a wrist, the wearable biosignal interface 100 may detect the second signal generated by the muscle contraction or muscle relaxation of the wrist.

The target 105 may be, for example, a wrist, a forearm, a face, a neck and the like of a living being. The body part may include a muscle that generates the second signal.

The biosignal sensor 120 may include at least one biosensor detecting the second signal from a muscle of the target 105 and may monitor contraction or relaxation of the muscle. The biosensor may be a photo sensor, a piezoelelctric sensor, a force sensor, an EMG sensor, and the like by using the at least one biosensor.

For example, the biosignal sensor 120 may include the photo sensor. Using the photo sensor, the wearable biosignal interface 100 may obtain the second signal associated with a state of the target 105, based on light scattering.

The biosignal sensor 120 may include a piezoelelctric sensor or a force sensor. Using the piezoelelctric sensor or the force sensor, the wearable biosignal interface 100 may obtain the second signal associated with an extension and/or contraction state of the target 105.

The biosignal sensor 120 may include an EMG sensor. Using the EMG sensor, the wearable biosignal interface 100 may obtain the second signal associated with a muscle contraction or relaxation of the target 105.

The biosignal sensor 120 may be affixed to a bracelet fastened onto the target 105, along with a motion sensor 110, as illustrated in FIG. 1. In this example, a sensing surface of the biosignal sensor 120 may be affixed to the bracelet to be in a direct contact with the skin of the target 105. On the sensing surface, one or more biosensor may be arranged to detect a second signal generated from the target 105. For example, the bracelet may detect, using the biosignal sensor 120, various forms of second signals such as a bio-electric/magnetic signal, a bio-impedance signal, and a bio-mechanical signal associated with the target 105.

The bracelet may be fastened onto the target 105, wrapping around the skin that covers a wrist muscle. For example, the bracelet may be fastened onto the target 105 by covering the wrist muscle with a specialized area such as the sensing surface of the bracelet on which the one or more biosignal sensor 120 is disposed. Using the one or more biosensor, the biosignal sensor 120 may collect the second signal throughout an entire area of the wrist muscle of the target 105.

In 430, the wearable biosignal interface 100 may determine a validity of the second signal based on the first signal. In 430, the wearable biosignal interface 100 may determine whether the second signal is generated by an intentional motion of the target 105 or incidentally generated by an unintentional or spontaneous motion of the target 105.

The wearable biosignal interface 100 may determine the second signal to be valid in the event that the magnitude of the first signal satisfies a first threshold value.

Here, the first threshold value may be a reference value used to determine the intentional motion of the target 105. The first threshold value may be determined as an average value of magnitudes of the first signals obtained while a user moves a muscle for an actual operation.

The wearable biosignal interface 100 may determine the first threshold value based on a magnitude of the second signal to be obtained. For example, the wearable biosignal interface 100 may determine the first threshold value for operation involving a large motion of the target 105 to be greater in proportion to the magnitude of the second signal; thus, the second signal generated by the intentional motion of the target 105 may not be ignored due to a threshold value determined to be small.

The wearable biosignal interface 100 may determine the first threshold value for a quick display shift operation of a display apparatus for which a relatively greater second signal is generated to be greater than the first threshold value for an ON/OFF operation of an illumination apparatus for which a relatively smaller second signal is generated.

To determine a validity of the second signal, the wearable biosignal interface 100 may identify interval during which the magnitude of the first signal is less than or equal to the first threshold value and may determine a signal, among the second signals, obtained in the identified interval to be a valid second signal. The wearable biosignal interface 100 may determine the second signal obtained in the interval during which the magnitude of the first signal is less than or equal to the first threshold value and a small motion of the target 105 is determined to be valid.

The wearable biosignal interface 100 may determine the second signal to be invalid, irrespective of the first signal, in the event that the magnitude of the obtained second signal does not satisfy a second threshold value. The second threshold value may be a reference value used to determine the second signal that is valuable as information. The second threshold value may be determined as an averaged minimum value obtained a user moves a muscle for an actual operation. For instance, the second threshold value may be determined from historic values obtained based on many actual operations performed by a target.

In the event that the magnitude of the obtained second signal is less than or equal to the second threshold value, the wearable biosignal interface 100 may determine whether the target 105 moved intentionally for operation to be indefinite and accordingly, invalidate the second signal. Conversely, in the event that the magnitude of the second signal is greater than the second threshold value, the wearable biosignal interface 100 may further determine whether the magnitude of the first signal satisfies the first threshold value and may determine the validity of the second signal.

Based on a result of the determination, in the event that the second signal is determined to be valid, the wearable biosignal interface 100 may operate in an active mode and may allow an external device to be controlled by the second signal. The external device may be a general term for devices controlled by a command signal, such as a mobile device, a TV screen, a DVD player, a radio, a heating thermostat, a vehicle door, and the like. Using the wearable biosignal interface 100, the command signal may be generated based on the valid second signal.

For example, in the event that the magnitude of the first signal is less than or equal to the first threshold value, and the magnitude of the second signal exceeds the second threshold value, the wearable biosignal interface 100 may shift a mode of the wearable biosignal interface 100 to the active mode and may allow the external device to be controlled based on the second signal; thus, the accuracy in determining an intention of a user may be improved.

To control the external device after the shift to the active mode, the wearable biosignal interface 100 may transmit the command signal based on the valid second signal to an appliance such as a TV, an air conditioner, a computer, a refrigerator, and the like, or to a living environment controlling device such as a light, a curtain, a window, a door lock device, and the like. The transmission of the commend signal enables the external device to perform a control operation such as an ON/OFF operation and an open/close operation, requested by the command signal.

The wearable biosignal interface 100 may use the valid second signal as a signal for a remote controller of a vehicle to start the vehicle, or as an identification (ID) signal to make a payment.

The wearable biosignal interface 100 may use the valid second signal as a signal for interactive control of a computer, or to edit a file stored on the computer or move a page for a presentation.

The wearable biosignal interface 100 may invalidate a biosignal generated by the unintentional or spontaneous motion of the target 105 to optimally avoid a control error for the external device.

The wearable biosignal interface 100 may identify a biosignal exclusively generated during the state in which the target 105 is in a certain level of stability and may use the biosignal to control the external device. By using the biosignals genereated during a stable state, it is possible to determine an intention of a user with improved precision.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of non-transitory computer-readable storage media include magnetic media, such as hard disks, floppy disks, and magnetic tape; optical media such as CD ROM discs and DVDs; magneto-optical media, such as optical discs; and hardware devices that are specially configured to store and perform program instructions, such as read-only memory (ROM), random access memory (RAM), flash memory, and the like. Examples of program instructions include machine code, such as produced by a compiler, and files including higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. A wearable biosignal interface, comprising:
a motion sensor configured to obtain a first signal based on a motion of a target;
a biosignal sensor configured to be disposed on the target and obtain a second signal from the target; and
a determination controller configured to perform, in response to a magnitude of the first signal being less than or equal to a first threshold, a function of the wearable biosignal interface using a portion of the second signal corresponding to an interval during which the magnitude of the first signal is less than or equal to the first threshold.

2. The wearable biosignal interface of claim 1, wherein the determination controller is configured to determine the second signal to be valid in response to the magnitude of the first signal not satisfying the first threshold.

3. The wearable biosignal interface of claim 1, wherein the determination controller is configured to:
identify the interval during which the magnitude of the first signal is less than or equal to the first threshold; and
determine a signal, among a plurality of second signals obtained by the biosignal sensor in the identified interval, to be a valid second signal.

4. The wearable biosignal interface of claim 2, wherein the determination controller is configured to determine the first threshold based on a magnitude of the second signal.

5. The wearable biosignal interface of claim 1, wherein the determination controller is configured to determine the second signal to be invalid, irrespective of the first signal, in response to the magnitude of the second signal not satisfying a second threshold.

6. The wearable biosignal interface of claim 1, wherein:
in response to a determination to perform the function of the wearable biosignal interface, the determination controller is configured to perform the function; and
the function of the wearable biosignal interface includes the determination controller operating in an active mode to control an external device based on the second signal.

7. An operation method of a wearable biosignal interface, the method comprising:
using a motion sensor to obtain a first signal based on a motion of a target;
using a biosignal sensor disposed on the target to obtain a second signal; and
performing, in response to a magnitude of the first signal being less than or equal to a first threshold, a function of the wearable biosignal interface using a portion of the second signal corresponding to an interval during which the magnitude of the first signal is less than or equal to the first threshold.

8. The method of claim 7, wherein the determining of the validity comprises:
determining the second signal to be valid in response to the magnitude of the first signal not satisfying the first threshold.

9. The method of claim 7, wherein the determining of the validity comprises:
identifying the interval during which the magnitude of the first signal is less than or equal to the first threshold; and
determining a signal, among second signals obtained by the biosignal sensor in the identified interval, to be a valid second signal.

10. The method of claim 8, wherein the determining of the validity further comprises:
determining the first threshold based on a magnitude of the second signal.

11. The method of claim 8, wherein the determining of the validity comprises:
determining the second signal to be invalid, irrespective of the first signal, in response to a magnitude of the second signal not satisfying a second threshold.

12. The method of claim 7, further comprising:
operating in an active mode and controlling an external device based on the second signal, in response to the second signal being determined to be valid.

13. The wearable biosignal interface of claim 1, wherein the second signal includes biological information obtained by one or more biosensor in contact with skin of the target.

14. The method of claim 8, wherein the second signal includes biological information obtained by one or more biosensor in contact with skin of the target.

15. An apparatus comprising:
a motion sensor configured to detect a movement signal corresponding to a movement of a target;
a second sensor configured to detect a biological signal corresponding to a biological information of the target; and
a controller configured to:
determine an interval of stability in which a magnitude of the movement signal is less than or equal to a movement signal threshold,
determine a portion of the biological signal detected in the interval of stability, and
identify a command for controlling another device using the portion of the biological.

16. The apparatus of claim 15, wherein:
the interval is determined by extracting the movement signal based on the movement of the target; and
the biological signal is extracted from the biological information obtained by the second sensor, the second sensor comprising one or more biosensors.

17. The apparatus of claim 16, wherein the interval corresponds to a time duration in which the magnitude of the first processed signal is less than or equal to the movement signal threshold.

18. The apparatus of claim 16, further comprising a transmission unit configured to transmit the command to the another device, wherein the determination controller is configured to identify the command based on the portion of the biological signal.

19. The apparatus of claim 18, wherein, in response to a determination that the magnitude of the movement signal is greater than the movement signal threshold, the apparatus is configured not to transmit a command based on the portion of the biological signal.

20. The wearable biosignal interface of claim 1, wherein the determination controller is configured to perform the function based on a comparison between the first signal and a first threshold.

* * * * *